(12) United States Patent
Wieters et al.

(10) Patent No.: US 10,564,410 B2
(45) Date of Patent: Feb. 18, 2020

(54) ENDOSCOPE AND METHOD FOR ASSEMBLING AN ENDOSCOPE

(71) Applicant: OLYMPUS WINTER & IBE GMBH, Hamburg (DE)

(72) Inventors: Martin Wieters, Barsbuettel (DE); Lars Hansen, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 357 days.

(21) Appl. No.: 15/329,794

(22) PCT Filed: Jul. 24, 2015

(86) PCT No.: PCT/EP2015/001529
§ 371 (c)(1),
(2) Date: Jan. 27, 2017

(87) PCT Pub. No.: WO2016/020043
PCT Pub. Date: Feb. 11, 2016

(65) Prior Publication Data
US 2017/0261742 A1    Sep. 14, 2017

(30) Foreign Application Priority Data
Aug. 4, 2014   (DE) .......................... 10 2014 111 069

(51) Int. Cl.
*G02B 23/24*   (2006.01)
*A61B 1/07*    (2006.01)
(Continued)

(52) U.S. Cl.
CPC ........ *G02B 23/2469* (2013.01); *A61B 1/0008* (2013.01); *A61B 1/0011* (2013.01);
(Continued)

(58) Field of Classification Search
None
See application file for complete search history.

(56) References Cited

U.S. PATENT DOCUMENTS

| 4,576,147 A | 3/1986 | Hashiguchi |
| 4,850,342 A | 7/1989 | Hashiguchi et al. |

(Continued)

FOREIGN PATENT DOCUMENTS

| DE | 19720163 A1 | 11/1997 |
| DE | 102004023024 B4 | 3/2007 |

(Continued)

OTHER PUBLICATIONS

International Search Report dated Dec. 3, 2015 issued in PCT/EP2015/001529.

(Continued)

*Primary Examiner* — Michael Stahl
(74) *Attorney, Agent, or Firm* — Scully, Scott, Murphy & Presser, P.C.

(57) ABSTRACT

An endoscope optic including: an outer tube having an opening at an end face in an end region of the outer tube, a fiber tube disposed in the opening, the fiber tube containing an objective lens, and a fiber bundle for illuminating a region in front of the objective lens, the fiber bundle being provided at an outer periphery of the objective lens, wherein a distal end region of the fiber bundle being arranged in a distal aperture in the fiber tube, the aperture being surrounded by material of the fiber tube.

9 Claims, 3 Drawing Sheets

(51) Int. Cl.
*A61B 1/00* (2006.01)
*A61B 1/06* (2006.01)
*G02B 23/26* (2006.01)

(52) U.S. Cl.
CPC ...... *A61B 1/00096* (2013.01); *A61B 1/00179* (2013.01); *A61B 1/0623* (2013.01); *A61B 1/07* (2013.01); *G02B 23/243* (2013.01); *G02B 23/2476* (2013.01); *G02B 23/26* (2013.01)

(56) References Cited

U.S. PATENT DOCUMENTS

| | | | |
|---|---|---|---|
| 5,305,736 A | | 4/1994 | Ito |
| 5,700,236 A | | 12/1997 | Sauer et al. |
| 5,782,751 A | | 7/1998 | Matsuno |
| 6,004,263 A | * | 12/1999 | Nakaichi ............ A61B 1/00165 600/120 |
| 6,101,703 A | * | 8/2000 | Odanaka .................. A61B 1/07 29/447 |
| 6,248,060 B1 | | 6/2001 | Buess et al. |
| 2005/0250992 A1 | | 11/2005 | Scherr |
| 2007/0118013 A1 | * | 5/2007 | Miyagi .............. A61B 1/00096 600/129 |

FOREIGN PATENT DOCUMENTS

| | | |
|---|---|---|
| DE | 102007002042 B4 | 9/2008 |
| DE | 102013112282 A1 | 1/2014 |
| JP | S58-12642 A | 1/1983 |
| JP | H04-006513 A | 1/1992 |
| JP | H04-240434 A | 8/1992 |
| JP | H07-181398 A | 7/1995 |
| JP | 2001-292954 A | 10/2001 |
| WO | WO 98/06318 A1 | 2/1998 |

OTHER PUBLICATIONS

English translation of International Preliminary Report on Patentability dated Feb. 7, 2017 together with the Written Opinion received in related International Application No. PCT/EP2015/001529.

* cited by examiner

ENDOSCOPE AND METHOD FOR ASSEMBLING AN ENDOSCOPE

CROSS-REFERENCE TO RELATED APPLICATION

The present application is based upon and claims the benefit of priority from PCT/EP2015/001529 filed on Jul. 24, 2015, which claims benefit to DE 10 2014 111 069.2 filed on Aug. 4, 2014, the entire contents of each of which are incorporated herein by reference.

BACKGROUND

Field

The present disclosure generally relates to endoscopes, and more particularly to an endoscope and to a method for assembling an endoscope.

Prior Art

Endoscopes are used to observe a field of view, to which access is typically only enabled through a small opening. The endoscope has an endoscope optic with a lens. The endoscope optic can be formed as a separate component of the endoscope and inserted into the endoscope. In endoscopes, optical fibers are used to illuminate the field of view. For this purpose, a bundle of many optical fibers, i.e. a fiber bundle, is typically used to provide a sufficient light intensity. The fibers radiate the light at its end region in a relatively wide range of angles. Nevertheless, all fibers should preferably be oriented with their (main) beam direction towards the field of view. Other fibers provide disturbing brightness variations in the field of view. The fibers receive their appropriate orientation during the assembly of the endoscope optics. For sealing and fixing their orientation, the fibers at the distal end region are bonded with an adhesive and then polished.

DE 10 2004 023024 B4 introduces an obliquely-viewing endoscope with an endoscope optic which has a lens that is directed angled downward towards the longitudinal axis of the endoscope optic axis. In such endoscope optics, optical fibers are arranged laterally next to the actual optics and above. The laterally arranged fibers are oriented parallel to the viewing direction of the lens looking obliquely downward. The upper fiber bundle extends on the other hand parallel to the longitudinal extension of the endoscope optics. The optic fibers are arranged between an outer casing tube or outer tube and an inner fiber tube. The fiber tube contains inside the actual optics with the distal lens obliquely looking downward. Recesses are provided on the outer region of the fiber tube to orient the optical fibers and fix them in their position. The optical fibers are inserted into these recesses, before the outer tube is then pulled over the distal end region of the endoscope optics. The optical fibers are pressed and oriented through the outer tube into the recesses of the fiber tube. Then the optical fibers at the end region of the endoscope optics can be bonded together, cut and polished on the end face.

U.S. Pat. No. 4,850,342 introduces an endoscope optic in which a fiber channel is provided between the fiber tube and outer tube, which enables an orientation of the ends of the optical fibers in the end region through assembling the outer tube and fiber tube.

U.S. Pat. No. 4,576,147 also relates to an endoscope optic in which an orientation through formation of a fiber channel between an inner fiber tube and an outer tube is only achieved upon assembly of the endoscope optic.

A disadvantage of the known endoscope optics is that the final orientation of the optical fibers is only set with the final positioning of the outer tube as casing of the fiber tube. The assembly is therefore very complex and is to be performed manually.

SUMMARY

An object is to create a generic endoscope with optical fibers illuminating the field of view in a targeted manner, in which the assembly is facilitated and the orientation improved.

Such object can be achieved through an endoscope in which the distal end region of the fiber bundle is arranged in a distal aperture in the fiber tube of the endoscope optic. The aperture can be completely surrounded by material of the fiber tube, such as having an enclosed edge. In such configuration, the fiber tube has an aperture into which the optical fibers can be inserted. The aperture can pass through a wall of the fiber tube in a region with a thickening. The aperture can pass through the end face and/or at least a partial section of the end face of the fiber tube. The aperture can be adapted to receive the entire fiber bundle. By inserting the optical fibers into the aperture of the fiber tube, the fibers are already oriented, such as at their distal end regions. A correct orientation of the fiber ends is thereby only achieved in the fiber tube, without a slipping of the casing tube being necessary. The assembly of the endoscope is thus greatly facilitated.

The optical fibers or fiber bundle can be attached in the aperture. For this purpose, the optical fibers can be attached, for example, by a clamping effect, by frictional forces and/or a canting. This attachment serves, for example, to prevent a slippage of the optical fibers during assembly of the endoscope optic, for example, during assembly of the casing tube. The attachment can take place permanently. For this purpose, an adhesive or the like can be used to achieve a permanent fixing and sealing.

The lens can be oriented obliquely downward looking through the opening at an angle to the longitudinal axis of the fiber tube. Such an obliquely-looking endoscope can be used to observe a field of view lying away from the central longitudinal axis of the endoscope. This offers the advantage of an optimized field of view illumination. At the same time, an improved assembly of the endoscope or the endoscope optic is ensured.

The longitudinal axis of the aperture and the longitudinal axis of the distal end of the fiber bundle or the optical fibers can be oriented at least substantially parallel to each other. The longitudinal axis of the distal end of the fiber bundle can correspond to the beam direction of the optical fibers. In such configuration, the aperture can define the orientation of the distal end of the fibers. A clean guidance of the fibers is facilitated by the parallel or at least almost parallel orientation of the longitudinal axis of the fiber bundle and viewing direction of the lens. For this purpose, the aperture can have a sufficient longitudinal extent, in order to achieve a sufficient guidance of the fiber bundle. The aperture can be accordingly arranged extending obliquely with respect to the longitudinal axis of the fiber tube.

The orientation of the fiber bundle, such as its longitudinal axis or beam direction, can differ from the longitudinal axis of the aperture. This can be caused, for example, by a bending of the fibers. Such a bending can occur with an orientation of the end regions of the fibers, obliquely to the longitudinal extension of the endoscope optic. The oblique orientation can be provided for better illumination of the field of view. The bending of the fibers can take place in a bending region. Small deviations between the orientation of the aperture and the fiber ends can be compensated, for example, by a pre-tension.

The longitudinal axis of the aperture and the viewing direction of the lens or the longitudinal axis of the fiber bundle can enclose an acute angle in the region in front of the lens. In such configuration, the aperture or the fibers can be oriented somewhat more obliquely with respect to the longitudinal axis of the endoscope than the lens or its viewing direction. An improved orientation of the fibers in the desired direction is thus achieved. The desired direction can be parallel to the viewing direction of the lens for optimal illumination of the field of view, such as in a region close in front of the lens. The main direction of the aperture can be oriented more obliquely than that of the lens. In such configuration, the curved fibers can obtain an optimal arrangement. This can be advantageous, since optical fibers with a curved arrangement typically differ from the ideal orientation.

The angle between the longitudinal axis of the aperture or of the fiber bundle, such as its beam direction, and the field of view of the lens can be less than 20°, such as between 1° and 20°, such as between 2° and 6°. Such a slightly stronger tendency can be sufficient to compensate for a corresponding bending back of the fibers. Thus, an optimal illumination of the field of view can be achieved.

The aperture can be formed at least substantially as a semi-circular or crescent-shaped milling groove. Such a geometric shape offers a broad field of illumination with, at the same time, optimum adaptation to the generally circular outer shape of the endoscope optic. At the same time, the available space can be optimally utilized. The aperture can be provided above the optic or the lens.

The fiber bundle can end with the distal end region in the aperture. Likewise, the fiber bundle may be flush with the front edge of the fiber tube. Both orientations can cause the distal end region of the fiber bundle or the optical fibers to be arranged at an optimal position. At the same time, the greatest possible protection of the sensitive end face of the fibers may be achieved.

Finally, a method for producing or assembling an endoscope or an endoscope optic for an endoscope, is also provided. The method includes disposing the fiber bundle into the aperture in the fiber tube, while the distal end region of the fiber bundle is disposed in the aperture, inserting the fiber tube into the outer tube, to position the fiber bundle relative to the fiber tube and outer tube, and fixing the fiber bundle in the aperture. Such method can further include smoothing and/or polishing an end face side of the fiber bundle.

Such method simplifies the assembly considerably compared to the prior art. Here, the fiber bundle or the optical fibers are already oriented when inserted into the aperture of the fiber tube. The assembly of the outer tube or casing tube no longer affects the orientation of the fibers in practice. At most, the fiber bundle is provided with an additional fixing in the region between the fiber tube and the casing tube or outer tube.

Both straight-viewing and obliquely-viewing endoscopes can be utilized in the endoscope optic and methods described above.

BRIEF DESCRIPTION OF THE DRAWINGS

An embodiment will be described in more detail below with reference to the figures of the drawings.

DETAILED DESCRIPTION

Figure 1:
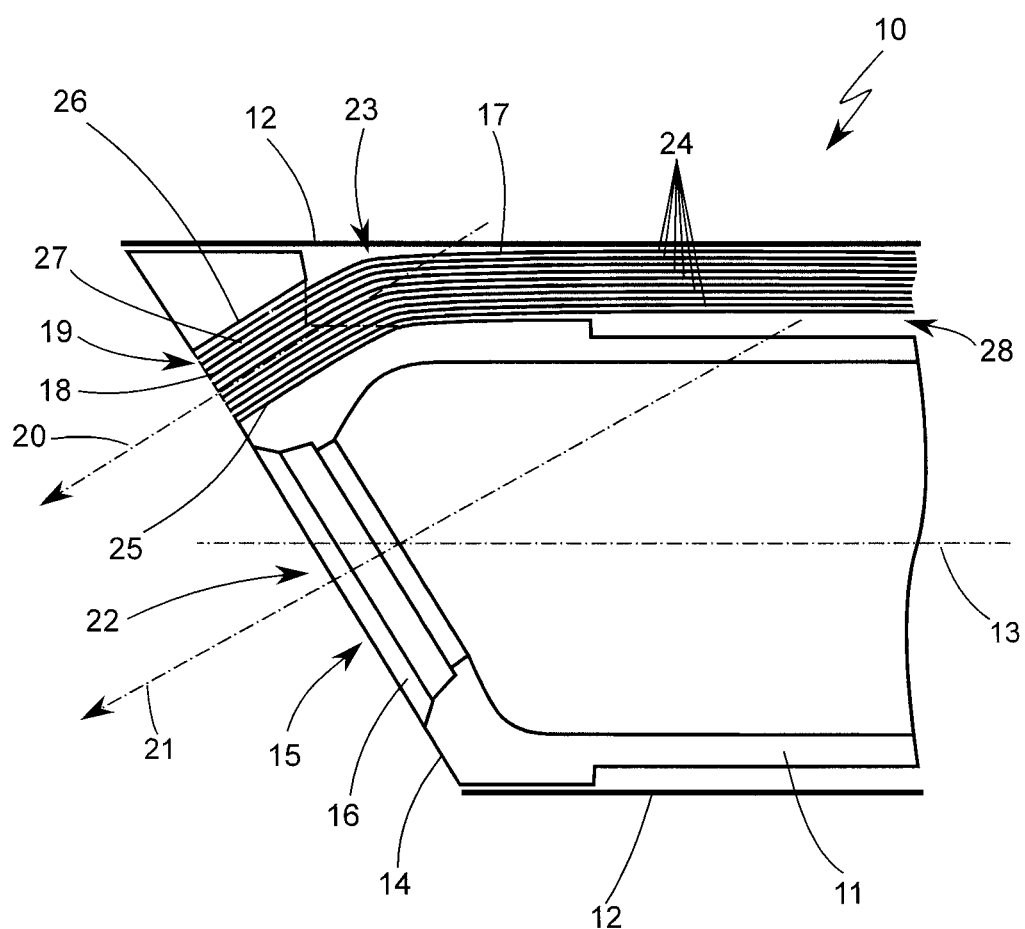
FIG. 1 illustrates a lateral sectional view of an endoscope optic for an endoscope in the assembled state.
Figure 2:
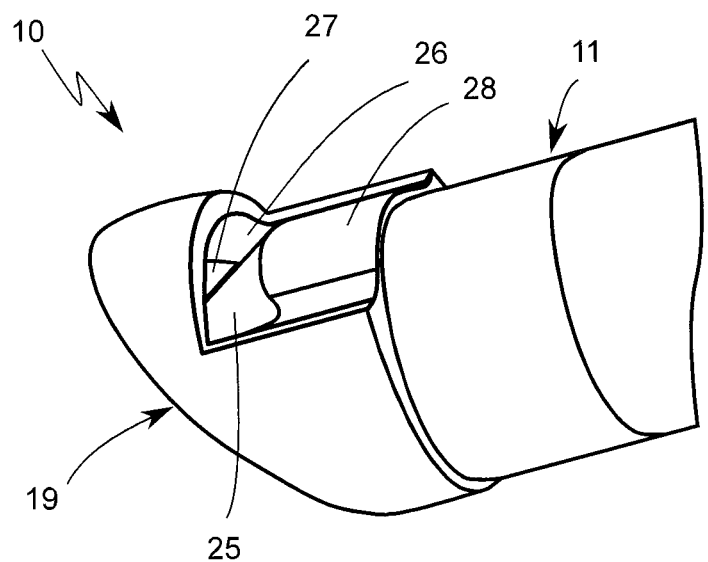
FIG. 2 illustrates a perspective rear view of a fiber tube of the endoscope optic.
Figure 3:
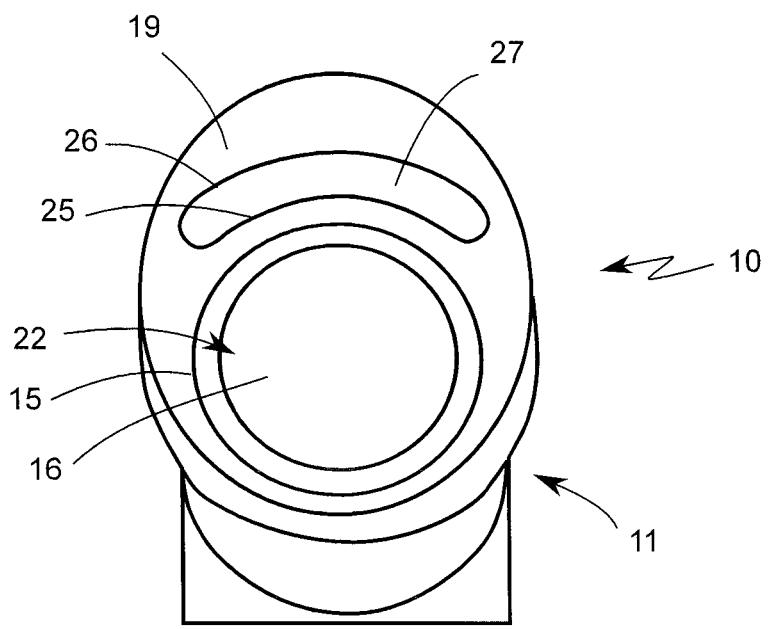
FIG. 3 illustrates a front view of the lens of the endoscope optic.

FIGS. 1-3 show an endoscope optic 10 for an endoscope in the assembled state in a lateral sectional view. Such an endoscope optic 10 is inserted into an endoscope not illustrated here and thus used in combination. For this purpose, the endoscope has a corresponding receptacle for the endoscope optic 10.

The endoscope optic 10 has a fiber tube 11, which is surrounded by an outer tube 12. The end face 14 of the endoscope optic 10 is arranged obliquely to the longitudinal axis of the endoscope optic 10. This end face 14 has an opening, such as a window opening 15, which is configured, for example, to receive a circular window 16. An optic system is provided inside the fiber tube (not illustrated). The viewing direction of the optic system is obliquely orientated in a direction 21 relative to a longitudinal axis 13 of the fiber tube 11.

The casing tube or outer tube 12 surrounds the entire endoscope optic 10 at least in the distal region, with the exception of the end face 14. A fiber bundle 17 is arranged in the upper region of the endoscope optic 10. The fiber bundle 17 ends at a distal end region with fiber ends 18 at the end face 14 of the endoscope optic 10. The fiber ends 18 meet substantially at least in an almost right angle to the end face 14. At the proximal end region of the fiber bundle 17, coupled light passes through the fiber bundle 17 and exits from its end face 19 to illuminate the field of view of the endoscope optic 10.

The endoscope optic has an objective lens 22 in the region of the window opening 15. The angle at which the objective lens 22 is oriented with its viewing direction 21 can, for example, be approximately 30°. This angle can be chosen depending on the scope of application of the endoscope optic 10. The end face 14 with the window 16 built into the window opening 15 is generally arranged at the same angle. Optionally, a straight-viewing optic can also be used instead.

The light output from the fiber end 18 thus extends mainly in a beam direction 20. The optic or the objective lens 22 looks accordingly in a viewing direction 21. In order to achieve sufficient illumination of the field of view of the optic, the beam direction 20 and the viewing direction 21 are arranged at least substantially parallel to each other. In order to achieve a better illumination directly in front of the objective lens 22 of the optic, the beam direction 20 can be arranged slightly inclined with respect to the viewing direction 21. In this case, the beam direction 20 and the viewing direction 21 intersect in the region in front of the end face 14 of the endoscope optic 10 at an acute angle. The angle is typically less than 20°, such as less than 10°, or between 2° and 6°.

As shown in FIG. 1, the fiber bundle 17 extends for the most part in a straight line and parallel to the longitudinal axis 13 of the endoscope optic 10. Only in the distal end portion thereof does the fiber bundle 17 extend in the beam direction 20 to illuminate the field of view.

In order to achieve an orientation of the fiber ends 18 to illuminate the field of view of the objective lens 22, the fiber bundle 17 undergoes a bending in a bending region 23. The fiber bundle 17 consists of a plurality of individual optical fibers 24, which can be bent in a simple manner accordingly. The fibers 24 extend parallel to each other.

The optical fibers 24 of the fiber bundle 17 are held for bending between a lower contact surface 25 and an upper contact surface 26 of an aperture 27 in the fiber tube 11. The lower contact surface 25 is, as in the prior art, a component of the fiber tube 11.

In the prior art, however, the upper contact surface 26 is attached to the outer tube 12. Accordingly, the distance between the lower contact surface 25 and the upper contact surface 26 can be increased for the assembly by sliding the outer tube 12 with respect to the fiber tube 11 in the prior art. The assembly is then performed by sliding the fiber tube 11 and outer tube 12 together in the correct position.

However, according to the embodiment of FIGS. 1-3, both the lower contact surface 25 and the upper contact surface 26 are part of the fiber tube 11. For this purpose, the aperture 27 is provided in the fiber tube 11. The aperture 27 can be configured as an arcuate slot or opening. It thus forms the lower contact surface 25 and the upper contact surface 26 for the optical fibers 24.

Figure 4:
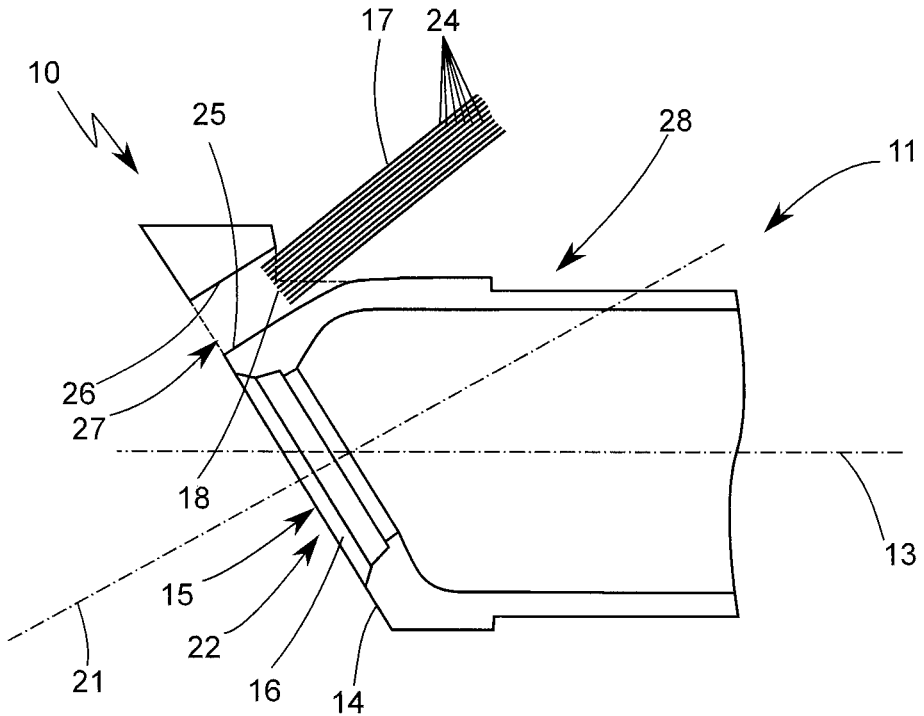
FIG. 4 illustrates a lateral sectional view of the endoscope optic during the insertion of the fiber bundle.
Figure 5:
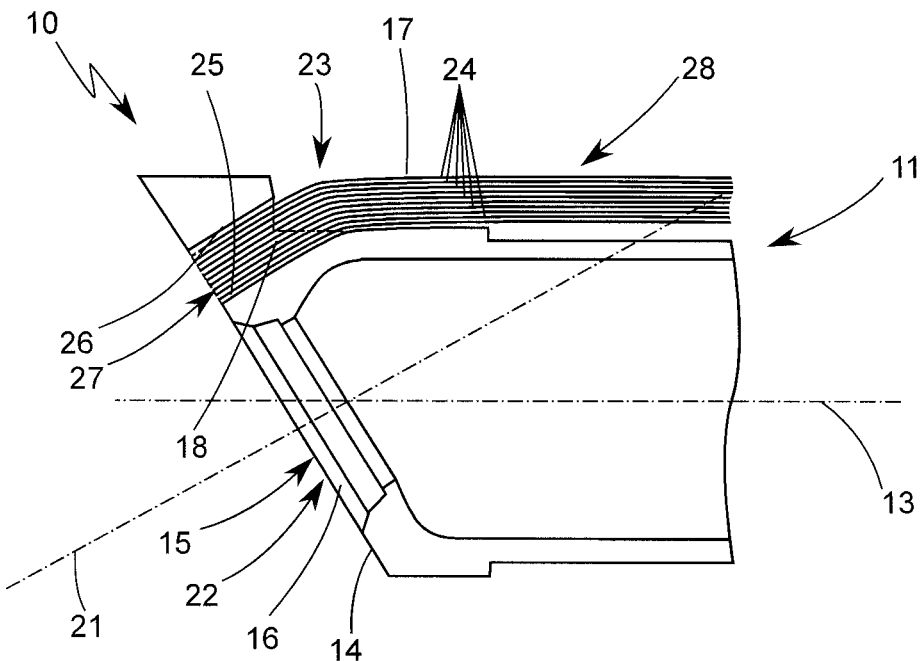
FIG. 5 illustrates a lateral sectional view with the inserted fiber bundle.

Referring now to FIGS. 4 and 5, a method for assembling the endoscope optic is as follows:

The optical fibers 24 of the fiber bundle 17 are inserted into the aperture 27 of the fiber tube 11, as is illustrated in FIG. 4. The introduction of the fiber bundle 17 can take place along more or less a straight route.

For further assembly, as illustrated in FIG. 5, the optical fibers 24 of the fiber bundle 17 are then bent downward somewhat and deposited on the top of the fiber tube 11. This results in a bending of the fibers 24 in the region of the bending point 23 due to a curved transition region provided in this region. This region is located between the lower contact surface 25 and a recess on the fiber tube side as part of a fiber channel 28 to receive the optical fibers 24. This fiber channel 28 is formed after the complete assembly of the endoscope optic 10 on the one hand by the top of the fiber tube 11 and on the other hand by the inside of the outer tube 12. While the optical fibers 24 of the fiber bundle 17 are guided into the interior of the fiber channel 28, the bending is maintained at the bending point 23.

In addition, a fixed mounting of the optical fibers 24 is thus provided in the aperture 27. This takes place since the fibers 24 are curved and abut the fiber tube 11 or outer tube 12. To fix the optical fibers 24 in the aperture 27, the optical fibers 24 are usually also molded in position by an adhesive. In addition, fiber ends 18 protruding beyond the end face 14 are cut and provided with a polishing in the plane of the end face 14. An end face 19 (see FIG. 1) of the fibers 24 is thus formed. This can be in a plane with the end face 14.

The fiber channel 28 can provide sufficient space for a more or less loose guidance of the optical fibers 24 of the fiber bundle 17. Meanwhile, the optical fibers 24 in the aperture 27 can be composed narrow, so that a stable orientation of the fiber ends 18 is thereby achieved.

The embodiments described above, as well as other embodiments, can be realized both with straight and obliquely-viewing endoscopes.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

LIST OF REFERENCE NUMERALS 10 endoscope optic
11 fiber tube
12 outer tube/casing tube
13 longitudinal axis
14 end face
15 window opening
16 window
17 fiber bundle
18 fiber ends
19 end face
20 beam direction
21 viewing direction
22 objective lens
23 bending region
24 optical fibers
25 lower contact surface
26 upper contact surface
27 aperture
28 fiber channel

What is claimed is:

1. An endoscope optic comprising:
   an outer tube having an opening at an end face in an end region of the outer tube,
   a fiber tube disposed in the opening, the fiber tube containing an objective lens, and
   a fiber bundle for illuminating a region in front of the objective lens, the fiber bundle being provided at an outer periphery of the objective lens,
   wherein a distal end portion of the fiber bundle being arranged in a distal aperture in the fiber tube, the aperture being surrounded by material of the fiber tube; and
   the fiber bundle having an other portion that is not arranged in the distal aperture, the other portion of the fiber bundle being arranged between an outer wall of the fiber tube and an inner wall of the outer tube;
   wherein a longitudinal direction of one or more of the aperture and a beam direction of the fiber bundle are set at an acute angle relative to a viewing direction of the objective lens such that they intersect in the region in front of the objective lens.

2. The endoscope optic according to claim 1, wherein the fiber bundle is attached to the aperture.

3. The endoscope optic according to claim 1, wherein the objective lens is oriented obliquely through the opening at an angle offset from a longitudinal axis of the fiber tube.

4. The endoscope optic according to claim 1, wherein the acute angle is between 1° and 20°.

5. The endoscope optic according to claim 1, wherein the aperture has one of a substantially semi-circular or crescent-shaped cross-section.

6. The endoscope optic according to claim 1, wherein the fiber bundle ends with one or more of the distal end portion in the aperture and the distal end portion being flush with one of the end face of the outer tube or an end face of the fiber tube.

7. A method for assembling the endoscope optic according to claim 1, the method comprising:
   disposing the distal end portion of the fiber bundle into the aperture in the fiber tube, while the distal end portion of the fiber bundle is disposed in the aperture, inserting the fiber tube into the outer tube to position the other portion of the fiber bundle relative to the fiber tube and outer tube such that the other portion of the fiber bundle is between the outer wall of the fiber tube and the inner wall of the outer tube, and fixing the distal end portion of the fiber bundle in the aperture.

8. The method of claim 7, further comprising, subsequent to the fixing, one of smoothing and polishing a distal end of the distal end portion of the fiber bundle.

9. The endoscope optic according to claim 4, wherein the acute angle is between 2° and 6°.

* * * * *